(12) United States Patent
Ali et al.

(10) Patent No.: US 9,801,908 B2
(45) Date of Patent: Oct. 31, 2017

(54) TREATMENT FOR CHITIN-CONTAINING MICROORGANISMS

(71) Applicant: BENCHMARK ANIMAL HEALTH LIMITED, Sheffield (GB)

(72) Inventors: Shimaa E. Ali, Cairo (EG); Even Thoen, Holter (NO); Ida Skaar, Lafayette, CA (US); Øystein Evensen, Lafayette, CA (US)

(73) Assignee: BENCHMARK ANIMAL HEALTH LIMITED, Sheffield (GB)

( * ) Notice: Subject to any disclaimer, the term of this patent is extended or adjusted under 35 U.S.C. 154(b) by 55 days.

(21) Appl. No.: 14/574,027

(22) Filed: Dec. 17, 2014

(65) Prior Publication Data

US 2015/0164944 A1 Jun. 18, 2015

Related U.S. Application Data

(60) Provisional application No. 61/917,608, filed on Dec. 18, 2013.

(51) Int. Cl.
*A61K 33/22* (2006.01)
*A61K 31/19* (2006.01)

(52) U.S. Cl.
CPC .............. *A61K 33/22* (2013.01); *A61K 31/19* (2013.01)

(58) Field of Classification Search
CPC ..... A61K 31/19; A61K 33/22; A61K 2300/00
See application file for complete search history.

(56) References Cited

U.S. PATENT DOCUMENTS 7,915,198 B2 * 3/2011 Kros .................... C05G 3/0064
423/325

* cited by examiner

*Primary Examiner* — Johann R Richter
*Assistant Examiner* — Genevieve S Alley
(74) *Attorney, Agent, or Firm* — Tian IP & Technology, LLC.

(57) ABSTRACT

The present disclosure relates to treatment of chitin-containing microorganism infection or colonization on an aquatic animal. The methods, systems, and kits provided herein facilitate termination and/or inhibition of proliferation of chitin-containing microorganisms (e.g., *Saprolegnia* and sea lice).

9 Claims, 10 Drawing Sheets

TREATMENT FOR CHITIN-CONTAINING MICROORGANISMS

CROSS REFERENCE TO RELATED PATENT APPLICATIONS

This application claims priority to U.S. Provisional Patent Application No. 61/917,608, filed on Dec. 18, 2013, entitled "Treatment for Chitin-Containing Microorganisms," which is hereby incorporated by reference in its entirety.

BACKGROUND

In general, aquatic animals (e.g., fish) are exposed to water with a high microorganism population. When microorganisms breach the physical and immune system of an aquatic animal, infectious diseases may result. In the wild, the Infectious diseases are normally at low levels because the water in which the animals live circulates freely. However, in a crowded and/or limited space (e.g., fish farms), such infection can become epidemics and the infectious diseases may be transferred to wild animal populations. In aquaculture industry, infectious diseases cause huge economic losses, such as, in fish and ova.

Therefore, there is a need in the art for rapid and effective treatment of a microorganism infection to save individual aquatic animal and to prevent the spread of disease to healthy animals.

SUMMARY

Embodiments of the present disclosure relate to methods for administering an anti-microorganism composition to an aquatic animal to treat chitin-containing microorganism infection or colonization. The methods may include dissolving an anti-microorganism composition in a carrier to give an anti-microorganism solution, and contacting an aquatic animal with the anti-microorganism solution. The anti-microorganism composition may include boric acid (BA).

Embodiments of the present disclosure also relate to kits for administering an anti-microorganism composition to an aquatic animal to treat chitin-containing microorganism infection or colonization. The kits may include a container having the anti-microorganism composition including boric acid (BA), and package material that may include instructions directing the administering the anti-microorganism composition to the aquatic animal to treat the chitin-containing microorganism infection or colonization. The anti-microorganism composition is dissolved in a carrier to give an anti-microorganism solution.

Embodiments of the present disclosure also relate to methods for treating chitin-containing microorganism infection or colonization on an aquatic animal. The methods may include contacting the aquatic animal with marine or freshwater containing BA in a sufficient quality to inhibit proliferation of the chitin-containing microorganism.

Embodiments of the present disclosure also relate to systems for farming an aquatic animal. The systems may include marine or freshwater containing BA in a sufficient quality to inhibit proliferation of chitin-containing microorganisms.

In some embodiments of the methods, kits, and/or systems of the present disclosure, the aquatic animal may be selected from the group consisting of a fish, an aquatic mammal, an aquatic bird, an aquatic reptile, an amphibian, and an aquatic invertebrate. In certain embodiments, the aquatic animal may be a fish. In particular embodiments, the fish may be a farmed fish including at least one of a brown trout, an Atlantic salmon, a rainbow trout, a coho salmon, a channel catfish, a pike, an arctic char, an eel, a roach, a carp, a sturgeon, a kissing gourami, a guppy, a swordfish, a tilapia, or a platyfish, or any fish kept as pet-fish in aquaria, or zebrafish kept in experimental units or as pet fish. In particular embodiments, the fish may include at least one of a fish egg, a Juvenile fish, a fry, a fingerling, an adult fish or an off-spring of the fish.

In some embodiments of the methods, kits, and/or systems of the present disclosure, the aquatic animal may have the chitin-containing microorganism infection or colonization. In certain embodiments, the chitin-containing microorganism infection may be associated with an oomycete including at least one of a *Saprolegnia*, an *Aphanomyces*, or *Branchiomyces*. In particular embodiments, the chitin-containing microorganism infection may be associated with a *Saprolegnia*. In certain embodiments, the chitin-containing microorganism infection may be associated with an ectoparasites. In particular embodiments, the ectoparasites comprises a sea louse. In these instances, the sea louse may be a sea louse of at least one of a genera *Lepeophtheirus, Caligus, Caligus rogercresseyi, Caligus clemensi, Caligus chiastos, Caligus epidemicus, Caligus elongates*, or *Lepeophtheirus salmonis*.

In some embodiments of the methods, kits, and/or systems of the present disclosure, the BA in the anti-microorganism solution may have a concentration in the anti-microorganism solution of between about 0.2 g/L and 1 g/L. In particular embodiments, the BA in the anti-microorganism solution may have a concentration in the anti-microorganism solution of between about 0.1 g/L and 0.2 g/L. In particular embodiments, the BA in the anti-microorganism solution may have a concentration in the anti-microorganism solution that is not less than about 0.2 g/L. In particular embodiments, the BA in the anti-microorganism solution may have a concentration in the anti-microorganism solution of between about 0.2 g/L and 0.5 g/L. In particular embodiments, the BA in the anti-microorganism solution may have a concentration in the anti-microorganism solution of between about 0.5 g/L and 1 g/L.

In some embodiments of the methods, kits, and/or systems of the present disclosure, the anti-microorganism solution may also contain (propionic acid) PA, and a concentration of PA in the anti-microorganism solution of not less than 0.2 g/L. In particular embodiments, the anti-microorganism solution may contain PA, and a concentration of PA in the anti-microorganism solution of between about 0.2 g/L and 1 g/L.

In some embodiments of the methods, kits, and/or systems of the present disclosure, the contacting the aquatic animal with the anti-microorganism solution may include contacting the aquatic animal with the anti-microorganism solution for a period of time of between about 24 hours and 96 hours. In particular embodiments, the contacting the aquatic animal with the anti-microorganism solution may include contacting the aquatic animal with the anti-microorganism solution for a predetermined number of times within 24 hours. In these instances, the predetermined number may be at least one of 1, 2, 3, 4, 5, 6, or 8.

In some embodiments of the methods of the present disclosure, the methods may include removing the aquatic animal from the anti-microorganism solution. In particular embodiments, the methods may also include contacting the aquatic animal with water not containing the anti-microorganism composition.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Overview

Figure 1:
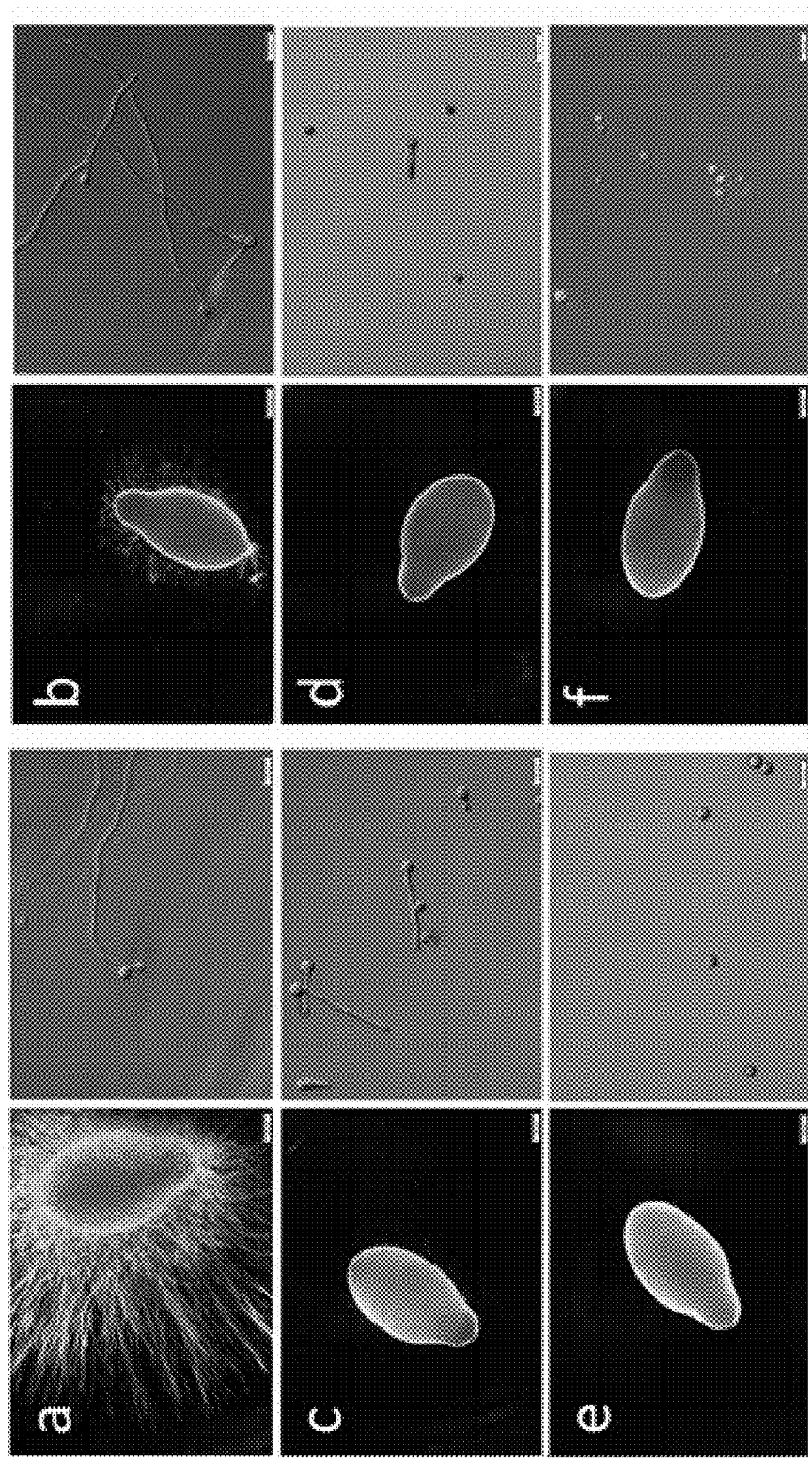
FIG. 1 shows effect of boric acid on the germination and colonization of *Saprolegnia* spores following 48 hours incubation.

Embodiments of the present disclose contemplate a use of boric acid (BA) or combination of boric acid and propionic acid (PA) for treating chitin-containing microorganism (e.g., *Saprolegnia*, sea lice, and etc.) infection or colonization. The present disclosure relates, in part, to the demonstration that boric acid or combination of BA and PA can inhibit germination and growth of *Saprolegnia* and decrease survival rates of sea lice. For example, as shown in the accompanying embodiments, BA may decrease *Saprolegnia* spore activity and mycelial growth in certain low concentrations, and completely inhibit germination and growth of *Saprolegnia* in certain high concentrations.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "aquatic animal" refers to any animal that spends all or some of the life in marine or fresh water. An "aquatic animal" can be, but is not limited to, a mammal such as a seal, sea lion, walrus, manatee, dugong, porpoise, dolphin, cetaceous or non-cetaceous whale, otter, or beaver; a bird such as, but not limited to, a web-footed bird such as a duck, goose, swan, gull, cormorant, penguin, a wading bird such as a coot, moor hen, flamingo, stork, heron; an aquatic reptile such as, but not limited to, an alligator, cayman, crocodile, turtle, snake or lizard; an amphibian such as, but not limited to, frogs, toads, newts and salamanders, neotenous larva or larvae thereof; fish and aquatic invertebrates such as, but not limited to, crustacea, insects, or molluscs.

The term "carrier" as used herein refers to any pharmaceutically acceptable solvent of antibiotics, chelating agents and pH buffering agents that will allow the antimicrobial composition of the present disclosure to be administered directly to an aquatic animal. A "carrier" as used herein, therefore, refers to such solvent as, but is not limited to, water, saline, physiological saline, ointments, creams, oil-water emulsions or any other solvent or combination of solvents and compounds known to one of skill in the art that is pharmaceutically and physiologically acceptable to the recipient animal. The term "carrier" further includes vitamin E or the like that may comprise an oily film over the site of application on the surface of an animal.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The term "derivative" is meant a chemical compounds (e.g., borates) that has been derived from the basic structure (e.g., boric acid) by any reaction, for example, by conjugation or complexing with other chemical moieties and/or structures.

The term "fish" refers to any marine or freshwater fish species maintained in a tank, aquarium, pool, pond, aquaculture facility, fish farm, or any means other than the natural environment of the fish species. The term "fish" also refers to species and individuals thereof captured, rescued or taken from their native habitat and which may require treatment for microbial infestations. Fish species to which the methods of the present disclosure may be applied include, but are not limited to, ornamental fish, zebrafish, goldfish, koi, oscar, cichlids, tropical fish and fish for human or animal food such as, but not limited to, catfish, and salmonids such as trout, or salmon. In addition, examples of fish may include a brown trout, an Atlantic salmon, a rainbow trout, a coho salmon, a channel catfish, a pike, an arctic char, an eel, a roach, a carp, a sturgeon, a kissing gourami, a guppy, a swordfish, or a platyfish. Fish also refers to a fish of different stages between birth and adulthood, for example, eggs, juvenile fish, growing fish or a mature fish.

The term "disease" as used herein refers to a pathological condition recognizable as an abnormal condition of an animal. A "fish disease" is a pathological condition of fish that may be fatal or benign such as, but not limited to, ulcers, fin rot, dropsy, Malawi bloat disease, gill disease and columnaris, *Saprolegnia* infections, see louse infections, or saddle-patch disease.

As used herein, the terms "function" and "functional" and the like refer to a biological, enzymatic, or therapeutic function.

The terms "modulating" and "altering" include "increasing" and "enhancing" as well as "decreasing," "inhibiting," or "reducing," typically in a statistically significant or a physiologically significant amount or degree relative to a control. In specific embodiments, anti-viral response level in response to viral infection is decreased relative to an unmodified or differently modified cell by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%.

An "increased" or "enhanced" amount is typically a "statistically significant" amount, and may include an increase that is 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000, 10 000 times or more) (including all integers and decimal points in between and above 1, e.g., 1.5, 1.6, 1.7, 1.8, etc.) an amount or level described herein.

A "decreased," "inhibiting," or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7, 1.8, etc.) an amount or level described herein. For example, In specific embodiments, germination or colonization associated with *Saprolegnia* spores in marine or freshwater containing BA is decreased relative to marine or freshwater without containing BA by at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, or at least 1000%.

The terms "marine" or "freshwater" refer to the natural environment of an aquatic animal. The term "marine" refers to any environment relating to the oceans or seas wherein the water is saline. The term "freshwater" refers to, but is not limited to, lakes, ponds, rivers, streams, brooks or any other low salinity water.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Substantially" or "essentially" means nearly totally or completely, for instance, 95%, 96%, 97%, 98%, 99% or greater of some given quantity.

As used herein, the term "treatment" is defined as the application or administration (e.g., a bath) of a therapeutic agent to a subject (e.g. a fish), or application or administration of the therapeutic agent to an isolated tissue (e.g., fish eggs) or cell line from a patient, who has a disease (e.g., *Saprolegnia* infections), a symptom of disease or a predisposition toward a disease, with the purpose to cure, heal, alleviate, relieve, alter, remedy, ameliorate, improve or affect the disease, the symptoms of disease, or the predisposition toward disease. For example, "treatment" of a subject in whom no symptoms or clinically relevant manifestations of a disease or disorder have been identified is preventive or prophylactic therapy, whereas clinical, curative, or palliative "treatment" of a subject in whom symptoms or clinically relevant manifestations of a disease or disorder have been identified generally does not constitute preventive or prophylactic therapy.

Treatment of *Saprolegnia* infections in a fish, for example, includes inhibiting or preventing colonization of infectious stages of *Saprolegnia* or killing of infectious and/or multiplying stages of *Saprolegnia* like hyphae. Treating *Saprolegnia* infections in a fish and preventing *Saprolegnia* infection progression can include alleviating or preventing symptoms, disorders or clinical disease associated with *Saprolegnia* infections, thereby curing an infection and restituting the health of the fish or through prophylactic treatment, prevent clinical manifestation of disease to occur. Each form of treatment may be considered a distinct aspect of the disclosure.

The term "chitin-containing microorganism infection" refers to any pathological or non-pathological presence of at least a chitin-containing microorganism on or in an aquatic animal, and which may be treated by an anti-microorganism composition containing bath or dip of the animal.

The term "chitin-containing microorganism colonization" refers to microorganisms carrying chitin (deacetylated chitosan) as part of their cell membrane or their exoskeleton.

The term "chitin-containing microorganism" refers to organisms carrying a coat, membrane, cell wall or exoskeleton containing chitin or chitosan-derived material, for example, *Saprolegnia* or Sea louse.

The term "microorganism" as used herein refers to any bacteria, fungus, oomycete or Arthropode, for example, *Saprolegnia* or Sea louse.

The term "boric acid" refers to an organic compound with the formula $H_3BO_3$ or any chemical compound containing parts or traces of $H_3BO_3$ The term "propionic acid" refers to an organic compound with the formula $CH_3CH_2COOH$ or any chemical compound containing parts or traces of propionic acid $CH_3CH_2COOH$.

Treating Chitin-Containing Microorganism Infection or Colonization Using BA or Combination of BA and PA Embodiments of the present disclosure relate to methods for administering an anti-microorganism composition to an aquatic animal to treat chitin-containing microorganism infection or colonization. The methods may include dissolving an anti-microorganism composition in a carrier to give an anti-microorganism solution, the anti-microorganism composition including boric acid (BA), and contacting an aquatic animal with the anti-microorganism solution.

Embodiments of the present disclosure also relate to kits for administering an anti-microorganism composition to an aquatic animal to treat chitin-containing microorganism infection or colonization. The kits may include a container having the anti-microorganism composition including boric acid (BA), the anti-microorganism dissolved in a carrier to give an anti-microorganism solution, and package material that may include instructions directing the administering the anti-microorganism composition to the aquatic animal to treat the chitin-containing microorganism infection or colonization.

Embodiments of the present disclosure also relate to methods for treating chitin-containing microorganism infection or colonization on an aquatic animal. The methods may include contacting the aquatic animal with marine or freshwater containing BA in a sufficient quality to inhibit proliferation of the chitin-containing microorganism.

Embodiments of the present disclosure also relate to systems for farming an aquatic animal. The systems may include marine or freshwater containing BA in a sufficient quality to inhibit proliferation of chitin-containing microorganisms.

In some embodiments, the aquatic animal may be selected from the group consisting of a fish, an aquatic mammal, an aquatic bird, an aquatic reptile, an amphibian, and an aquatic invertebrate. In certain embodiments, the aquatic animal may be a fish. In particular embodiments, the fish may be a farmed fish including at least one of a brown trout, an Atlantic salmon, a rainbow trout, a coho salmon, a channel catfish, a pike, an arctic char, an eel, a roach, a carp, a sturgeon, a kissing gourami, a guppy, a swordfish, or a platyfish or fish kept as pet-fish, or zebrafish kept as petfish or for medical research. In particular embodiments, the fish may include at least one of a fish egg, a Juvenile fish, a fry, a fingerling, an adult fish or an off-spring of the fish.

In some embodiments, the aquatic animal may have the chitin-containing microorganism infection or colonization. In certain embodiments, the chitin-containing microorganism infection may be associated with an oomycete including at least one of a *Saprolegnia*, an *Aphanomyces*, or *Branchiomyces*. In particular embodiments, the chitin-containing microorganism infection may be associated with a *Saprolegnia*. In certain embodiments, the chitin-containing microorganism infection may be associated with an ectoparasites. In particular embodiments, the ectoparasites comprises a sea louse. In these instances, the sea louse may be a sea louse of at least one of a genera *Lepeophtheirus, Caligus, Caligus rogercresseyi, Caligus clemensi, Caligus chiastos, Caligus epidemicus, Caligus elongates*, or *Lepeophtheirus salmonis*.

In some embodiments, the BA in the anti-microorganism solution may have a concentration in the anti-microorganism solution of between about 0.2 g/L and 1 g/L. In particular embodiments, the BA in the anti-microorganism solution may have a concentration in the anti-microorganism solution of between about 0.1 g/L and 0.2 g/L. In particular embodiments, the BA in the anti-microorganism solution may have a concentration in the anti-microorganism solution that is not less than about 0.2 g/L. In particular embodiments, the BA in the anti-microorganism solution may have a concentration in the anti-microorganism solution of between about 0.2 g/L and 0.5 g/L. In particular embodiments, the BA in the anti-microorganism solution may have a concentration in the anti-microorganism solution of between about 0.5 g/L and 1 g/L.

For instances, BA may decrease *Saprolegnia* spore activity and mycelial growth at concentrations more than 0.2 g/L, and BA may completely inhibit germination and growth of *Saprolegnia* at a concentration of 1 g/L. BA may also control saprolegniosis on Atlantic salmon eyed eggs at concentrations ranging from 0.2-1.4 g/L during continuous exposure, and at 1.0-4.0 g/L during intermittent exposure. BA may also control saprolegniosis on salmon yolk sac fry at a concentration of 0.5 g/L boric acid during intermittent exposure in response to a natural outbreak of saprolegniosis. For example, Treatment of sea lice copepodits with 0.4 g/L of boric acid may reduce swimming activity and lower survival rate of the sea lice.

In some embodiments, the anti-microorganism solution may also contain (propionic acid) PA, and a concentration of PA in the anti-microorganism solution of not less than 0.2 g/L. In particular embodiments, the anti-microorganism solution may contain PA, and a concentration of PA in the anti-microorganism solution of between about 0.2 g/L and 1 g/L.

In some embodiments, the contacting the aquatic animal with the anti-microorganism solution may include contacting the aquatic animal with the anti-microorganism solution for a period of time of between about 24 hours and 96 hours. In particular embodiments, the contacting the aquatic animal with the anti-microorganism solution may include contacting the aquatic animal with the anti-microorganism solution for a predetermined number of times within 24 hours. In these instances, the predetermined number may be at least one of 1, 2, 3, 4, 5, 6, or 8.

In some embodiments, the aquatic animal may be removed from the anti-microorganism solution. In particular embodiments, the aquatic animal may then contacted with water not containing the anti-microorganism composition.

Pathogenicity Associated with Chitin-Containing Microorganism

Chitin $(C_8H_{13}O_5N)$n is a long-chain polymer of a N-acetylglucosamine, derived from glucose. Chitin is the main component of the cell walls of fungi and oomycetes (e.g., *Saprolegnia* sp.) that infect freshwater fish, the exoskeletons of arthropods (e.g., crustaceans and copepods). For example, Caligidae parasites of fish (i.e., external parasites) can be found on mucus and skin of wild and farmed fish. The structure of chitin is comparable to the polysaccharide cellulose and forms crystalline nanofibrils. By function it may be compared to the protein keratin.

Chitin is the building block of exoskeletons that is the external skeleton that supports and protects the body of an animal like grasshoppers and cockroaches, crustaceans (e.g., crabs and lobsters), and arthropods (e.g., copepods). For example, arthropods may include Caligidae parasites of fish (e.g., sea louse (*Lepeophtheirus salmonis*) of salmonids and *Caligus* sp. of fish).

Exoskeletons contain rigid and resistant components that fulfil a set of functional roles including protection, excretion, sensing, support, feeding and acting as a barrier against desiccation in terrestrial organisms. Exoskeletons have a role in defense from pests and predators, support, and in providing an attachment framework for musculature. Exoskeletons contain in addition to chitin also calcium carbonate which makes them harder and stronger.

*Saprolegnia* spp. are generally termed "watermolds" and share common features with fungi and algae. The term saprolegniasis refers to any disease of fishes or fish eggs caused by species of the family Saprolegniaceae (Oomycotina). Symbiotic associations between fish and *Saprolegnia* spp. have been known for decades and the first description dates back to 1748 where saprolegniasis was reported in roach (*Rutilus rutilus* L.) in England. Since then saprolegniasis has been detected in a growing number of species in or on various fishes from all over the world. Particular interest has been paid from countries and regions with growing aquaculture industry since saprolegniasis causes high economic losses in fish and ova.

*Saprolegnia* infection is traditionally known as "fungal infection" in fish, and is typical seen in the freshwater stage of salmonids. *Saprolegnia* infections are visible to the naked eye as white patches on the skin of the fish or as "cotton wool" on fish eggs. The "fungal" patches may consist of one or more species of *Saprolegnia* and may become grayish due to the presence of bacteria and debris. The disease was previously controlled by the use of malachite green, an organic dye which has proved very efficient in controlling all infectious stages of *Saprolegnia* spp. The use of malachite green has been banned in Norway and other parts of the world due to its potential toxicological effects. This has increased the incidence of *Saprolegnia* infections in the aquaculture all over the world, resulting in huge economic losses.

*Saprolegnia* spp. belong to the class Oomycetes, which is a group of fungi-like pathogens in the kingdom Straminiphila. Oomycetes have their phylogenetic roots with the chromophyte algae (which includes the diatoms, chrysophytes and brown seaweeds) rather than with the main evolutionary line of chitin containing fungi. The Oomycetes are subdivided in orders and comprises several pests, like *Phytophthora infestans* causing the potato late blight, *Aphanomyces astasi* causing crayfish plaque, several fish pathogens from the genera *Aphanomyces*, *Achlya* and *Saprolegnia* and at least one species (*Pythium insidiosum*) with the potential of infecting humans and other mammals. In contrast to true fungi Oomycetes contain little chitin in their walls, which instead is composed mainly of β-1-3-glucans. Taxonomic classification of *Saprolegnia* is shown in Table 1.

TABLE 1

Taxonomic classification of *Saprolegnia*

| | |
|---|---|
| Kingdom | Straminiphila |
| Division | Oomycota |
| Class | Oomycetes |
| Order | Saprolegniales |
| Family | Saprolegniaceae |
| Genus | Saprolegnia |
| Species | 20-22 species of *Saprolegnia* |

*Saprolegnia* spp. are characterized by the growth of delicate, non-septate hyphae and asexual reproduction by secondary zoospore discharge one by one in rapid succession through one exit pore in the sporangium. There are 20-22 species of *Saprolegnia*, most of them saprophytic. However, 8-10 individual species have been implicated as causing saprolegniasis of salmonid fishes (Hughes 1994), including *S. australis*, *S. delica*, *S. diclina*, *S. ferax*, *S. monoica*, *S. parasitca*, *S. salmonis*, *S. shikotsuensis* and *S. tortulosa*. The most frequently examined and discussed *Saprolegnia* species are the fish pathogenic *Saprolegnia parasitica* and the less pathogenic species *Saprolegnia diclina*. Traditionally, *Saprolegnia* species are separated by the presence of sexual reproduction and characteristics of the gonads, i.e. the oogonia and the antheridia. However, the taxonomy is complex, and in particular the so-called "*Saprolegnia* parasitica-diclina complex" has led to a lot of confusion. *Saprolegnia* species that grows on fish as parasites do not normally produce sexual structures during laboratory conditions. Absence of sexual reproductive structures one of the primary distinguishing characteristics of *Saprolegnia* parasitica. The concept is that any *Saprolegnia* growing on a living fish, and not producing sexual reproductive structures, is, by definition, *Saprolegnia* parasitica. *Saprolegnia* species isolated from fish and with clusters of long-spines in the secondary zoospore should be termed *Saprolegnia* parasitica as a practical approach.

*Saprolegnia* is homothallic, meaning that one single individual contains both male and female sex organs. The male and the female sex organs, the antheridium and the oogonium, respectively, are developed from the hyphae. Meiosis occurs to produce male nuclei and female eggs. The antheridia grow toward the oogonia and produce fertilization tubes that penetrate the oogonia. Fertilization occurs when the male nuclei travel down these tubes to the female eggs and fuse with the female nuclei. This produces several thick-walled zygotes, called oospores. The number of oospores per oogonium is not constant, ranging from one to four in some species, to over forty in others. Each oospore germinates into a new hypha which will produce a zoosporangium. From the zoosporangium the asexual reproduction, which is the main type of reproduction, occurs. The pyriform primary zoospores, which are released from the zoosporangia are weak swimmers and function simply to disperse the spores from the immediate vicinity of the sporangium and parent colony. These primary zoospores settle down to produce 5-10 μm thin-walled cysts. This primary cyst acts as a miniature sporangium and releases a reniform secondary zoospore, which is the main motile stage. The secondary zoospore can maintain motility for many hours, even days, until it also encysts to produce a secondary cyst (syn. "encysted zoospore", "zoospore cyst" or "cystospore"). Then, they usually germinate into a new mycelium, on which sexual reproduction occurs, thus starting the reproduction cycle anew. The secondary cysts can also release new secondary-like zoospores which are able to encyst again. These repeated cycles of zoospore encystment and release of respectively secondary zoospores and cysts are called polyplanetism or repeated zoospore emergence. Polyplanetism contributes to the fungus' pathogenicity by helping it to make several attempts locating a suitable culture medium to live on before settling down for good. After they have encysted the secondary zoospores develop hairs for attachment. It has been suggested that these hairs are also used for buoyancy to decrease sedimentation rate and for fungal-host recognition response and are important for pathogenesis.

*Saprolegnia* spp. are distributed worldwide in rivers and freshwater reservoirs. Over the last decades, saprolegniasis have been reported frequently from literally all continents. International transfer of fish and eggs as part of the aquaculture industry is a possible risk factor when it comes to spread of different *Saprolegnia* species and strains throughout the world.

*Saprognia* infection is the single largest cause of economic losses in aquaculture and worldwide this disease is second only to bacterial diseases in economic importance.

Fifty percent per year losses have been reported in elver (*Angullia anguilla*) and in coho salmon (*Oncorhynchus kisutch*) culture in Japan. In the south-eastern United States, major financial losses occur in channel catfish farming due to a condition called "winter kill" caused by *Saprolegnia* infections.

On infected fish, *Saprolegnia parasitica* form cotton-wool-like tufts on the integument. The early lesions are grey-white in colour and normally appear as circular colonies. The lesions are not randomly located, as head, fins and gills are more susceptible to infection. However, moribund fish may in severe cases have as much as 80% of the body surface area covered by *Saprolegnia*. Virulent strains of *Saprolegnia* spp. can cause very high mortalities (up to 100%) in many different salmonid species, and hyphae from *Saprolegnia* spp. are usually restricted to the integument and superficial musculature.

Histopatological changes beneath the superficial mycelia mat include dermal necrosis and oedema during the early stage, and deeper myofibrillar necrosis and extensive haemorrhage in the more progressive lesions. The tissue damage is probably caused by extracellular enzymes secreted by the advancing hyphae including hyphae penetration of the basement membrane. To date, there is no evidence to indicate that any *Saprolegnia* species produces toxins which could cause cellular damage at sites remote from the sites of hyphal invasion. It is generally accepted that the ultimate cause of death is the severe haemodilution caused by haemorrhage and by the destruction of the water-proof properties of the fish integument. Fish with severe saprolegniasis appear lethargic, lose the ability to position in the water column and generally do not recover. *Saprolegnia* infections of salmonid eggs are primarily associated with the aquaculture industry where large numbers of eggs, often of variable quality and viability, are incubated at relatively high densities. Any dead eggs which are not removed from the incubation system are readily colonized by *Saprolegnia*, although this probably represents saprophytic colonisation by a range of fungi from the family Saprolegniaceae.

*Saprolegnia* spp. may infect both fish and ova of all types of salmonids. The economic importance of brown trout (*Salmo trutta*), Atlantic salmon (*Salmo salar* L.), rainbow trout (*Oncorhynchus mykiss* (Walbaum)) and coho salmon (*Oncorhynchus kisutch*) is the main reason that saprolegniasis has been subject to such strong focus in these species. However, *Saprolegnia* spp. can also infect a number of other teleost species. Channel catfish (*Ictalurus punctatus*) pike (*Esox lucius*), arctic char (*Salvelinus alpinus*) and eel (*Anguilla anguilla*) as well as roach (*Rutilus rutilus*), carp (*Cyprinidae* spp.) and sturgeon (*Acipenseridae* spp.) have been infected with *Saprolegnia*. It has also been associated with tropical fish, including the kissing gourami (*Helostoma temminckii*), guppy (*Poecilia reticulata*), swordfish (*Xiphias gladius*) and platyfish (*Xiphophorus couchianus*).

The sea louse (plural sea lice) is a copepod within the order Siphonostomatoida, family Caligidae. There are more than 550 species in 37 genera, including approximately 162 *Lepeophtheirus* and 268 *Caligus* species. Sea lice are marine ectoparasites (external parasites) that feed on the mucus, epidermal tissue, and blood of host marine fish. The genera *Lepeophtheirus* and *Caligus* parasitize marine fish, in particular those species that have been recorded on farmed salmon. *Lepeophtheirus salmonis* and various *Caligus* species are adapted to saltwater and are major ectoparasites of farmed and wild Atlantic salmon. Several antiparasitic drugs have been developed for control purposes. Since *L. salmonis* is the major sea louse of concern and has the most known about its biology and interactions with its salmon host. *Caligus* rogercresseyi has become a major parasite of concern on salmon farms in Chile. Recent evidence is also emerging that *L. salmonis* in the Atlantic Ocean has sufficient genetic differences from *L. salmonis* from the Pacific, showing that Atlantic and Pacific *L. salmonis* may have independently co-evolved with Atlantic and Pacific salmonids.

General understanding of the biology of sea lice is for the main part based on laboratory studies designed to understand issues associated with sea lice infecting fish on salmon farms. Information on sea lice biology and interactions with wild fish is unfortunately sparse in most areas with a long-term history of open net-cage development, since understanding background levels of sea lice and transfer mechanisms have rarely been a condition of tenure license for farm operators.

Many sea louse species are species specific, for example *L. salmonis* has high specificity for salmonids, like farmed Atlantic salmon (*Salmo salar*). *Lepeophtheirus salmonis* can to some degree parasitize other salmonids, like brown trout (sea trout, *Salmo trutta*), arctic char (*Salvelinus alpinus*), and Pacific salmon species. Pacific *L. salmonis* can also develop on three-spined stickleback (*Gasterosteus aculeatus*) the life-cycle will not be completed. Temperature, light and currents depend the survival of sea lice (at different stages). Sea lice cannot live in freshwater and die and fall off anadromous fish such as salmonids as they return to freshwater. Atlantic salmon migrate to and swim upstream in the fall to reproduce, while the smolts return to saltwater the second spring.

*Lepeophtheirus salmonis* is approximately twice the size of most *Caligus* spp. (e.g. *C. elongatus*, *C. clemensi*, etc.). The body of sea lice consists of 4 regions: cephalothorax, fourth leg-bearing segment, genital complex, and abdomen. All species of lice have mouth parts shaped as a siphon or oral cone. The second antennae and oral appendages are modified to hold the parasite on the fish (attached stages). The adult females are significantly larger than males and develop a large genital complex which makes up the majority of the body mass. Two egg strings of 500 to 1000 eggs that get darker as it matures are approximately the same length as the female's body.

Sea lice have both free swimming (planktonic) and parasitic life stages. All stages are separated by moults. Eggs hatch into nauplius I which moult to a second naupliar stage and these stages are non-feeding stages. The copepodids are the infectious stage and search for an appropriate host. Currents, salinity, light, and other factors will assist copepodids in finding a host and settlement on the fish occurs in areas with the least hydrodynamic disturbance, typically fins and other protected areas. Attached copepodids will be attached to a suitable host for a period of time before moulting is induced, to chalimus I stage. Sea lice continue their development through 2 chalimus stages separated by a moult. They are attached to the host during this period. The pre-adult and adult stages are mobile (on the fish) and can also move between host fish.

Sea lice cause physical and enzymatic damage at attachment sites resulting in abrasion-like lesions that vary in severity depending and size. It is not clear whether stressed fish are particularly prone to infestation. Sea lice infection causes a generalized chronic stress response in fish. This can decrease the immune responses and render fish more susceptible to other diseases. Infection also impacts growth.

The degree of damage is also dependent on the species of sea lice, the developmental stages that are present, and the number of sea lice on a fish.

Control of sea lice typically constitutes integrated pest management programs and these are recommended in Canada, Norway, Scotland, and Ireland, and also considered and partly implemented in Chile. Treatment of sea lice today includes chemical treatment with various compounds delivered in the water or via feed, cleaner fish and also other non-chemical treatment approaches (laser beads etc.).

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

Example 1

Boric Acid Inhibits Germination and Colonization of Saproleqnia Spores and has a Static Effect on Mycelium Growth BA ($H_3BO_3$, M 61.83 g/mol) was used as a source for borate to test its effect on the germination of Saprolegnia spores and the growth of Saprolegnia hyphae (in vitro). BA was also tested for control of Saprolegnia infection of eyed salmon eggs and yolk sac fry (in vivo) and its safety in vivo was also assessed. Propionic acid (PA; $CH_3CH_2COOH$) was included to assess the combined effect on germination of Saprolegnia spores and the growth of Saprolegnia hyphae (in vitro).

Three strains of Saprolegnia parasitica were used to evaluate the in vitro effect of the BA on germination and colonization of Saprolegnia spores and also anti-growth effects on hyphae/mycelium. Two strains (i.e., VIO 2736, VIO 5708) were isolated from Atlantic salmon (Salmo salar L.), the source of the third strain (i.e., VIO 5730) was natural biofilms collected from fish tanks holding Atlantic salmon.

BA was diluted to desired concentration in Sterilized Aquarium Water (SAW). It was tested initially at 0.01, 0.1 and 1.0 g/L to find out the preliminary minimum inhibitory concentration (MIC) intervals in vitro. Once the concentration range able to inhibit Saprolegnia spore germination and arrest hyphae growth was determined, the test intervals were narrowed down and concentrations between 0.1 and 1.0 g/L were tested at incremental increase of 0.1 g/L.

Sesame seeds were autoclaved at 121° C. for 20 min and cooled. Saprolegnia zoospores were produced according to the method described previously by Stueland et al. (2005). 400 µl of Saprolegnia spore suspension (1.0×104 spores/L) and 400 µl of each tested BA concentration were incubated with sesame seeds in 24-well, flat-bottom plates (CO-STAR®). Sterilized aquarium water (SAW) was used as a non-treated control and bronopol (Pyceze Vet.® 500 g bronopol/L) was used as a positive control. Each BA concentration and controls were tested in triplicates and incubated at 20° C. 24 hours later, plates were examined microscopically. The germination and colonization of Saprolegnia spores on sesame seeds were graded as shown in table 2.

TABLE 2

Grades for the germination and colonization of Saprolegnia spores on sesame seeds

| | |
|---|---|
| Grade 0: | no germination no growing mycelia on the sesame seeds |
| Grade 1: | germinating spores no growing mycelia on the sesame seeds |
| Grade 2: | germinating spores very few growing mycelia on the sesame seeds |
| Grade 3: | germinating spores profuse growing mycelia on the sesame seeds |

400 µl of Saprolegnia spore suspensions were incubated with sterile sesame seeds using flat-bottom microwell plates for 12 h at 20° C. The plates were observed microscopically to confirm the attachment of the spores to the sesame seeds and the presence of the early growing mycelia. BA was added at 12 h post infection of the sesame seeds at the same concentrations mentioned above to all tested plates except controls. Plates were incubated further at 20° C. SAW was used as non-treated control and bronopol as positive control. Plates were inspected microscopically after 24 h for advanced mycelial growth. Mycelial growth on the sesame seeds was graded as 0 for complete inhibition of the growth, and grade 1 for slight reduction on the growth or the presence of abundance of the growing mycelium on the sesame seeds.

Saprolegnia spores germinated and colonized sesame seeds in all groups at BA concentrations below 0.2 g/L, however, the growth rate was slow compared to the non-treated control even at this low concentration. When boric acid was combined with propionic acid (PA), complete inactivation was found. When BA concentrations of 1 g/L and above were used inoculated Saprolegnia spores did not germinate (FIG. 1). FIG. 1 demonstrates effect of boric acid on the germination and colonization of Saprolegnia spores following 48 hours incubation. FIG. 1(a) Grade 3: Profuse Saprolegnia hyphal growth on sesame seeds in the non-treated control group (water). FIG. 1(b) Grade 3: germinating spores with mycelial growth on the sesame seeds (boric acid<0.2 g/L). FIG. 1(c) Grade 2: reduced germination rate and minimal mycelial growth on the sesame seeds (boric acid 0.2-0.4 g/L). FIG. 1(d) Grade 1: germinating spores without growing mycelia on the sesame seeds (boric acid 0.5-0.9 g/L). FIG. 1(e) Grade 0: no germinating spores, no growing mycelia on the sesame seeds (boric acid g/L). FIG. 1(f) Grade 0: positive control group (bronopol), no spore germination with absence of the growing mycelia on sesame seeds.

The effect on mycelia growth was also testes. At concentrations above 0.5 g/L BA arrests mycelia and no further growth was observed. At concentrations of 0.5 g/L and below grade 1 hyphael growth was observed. When concentrations of 0.2 g/L boric acid was combined with 0.2 g/L of propionic acid (PA), complete arrest was observed. This may indicate a potentiating effect of the two treatments combined.

Example 2

Boric Acid Arrests Development of Saprolegnia Zoosporangia

Sesame seeds carrying Saprolegnia mycelium with zoosporangia were examined microscopically after their exposure to 1 g/L of BA treatments for 12 and 24 h. Boric acid (0.2 g/L) was also combined with propionic acid (PA) (0.2-1 g/L) for assessment of combined effects.

Figure 2:
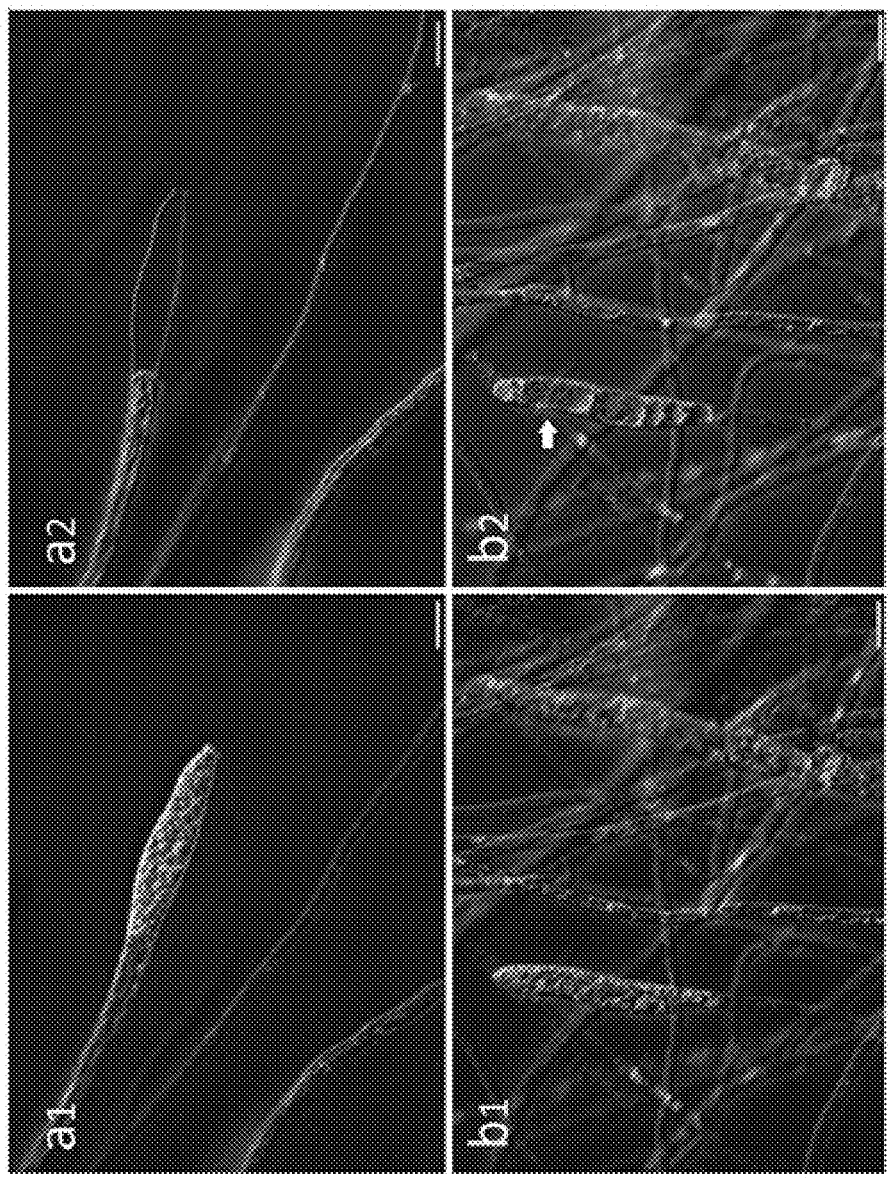
FIG. 2 shows *Saprolegnia* zoosporangia in the non-treated control before (a1) and after (a2) spore release. *Saprolegnia* zoosporangia before (b1) and after 24 hours exposure to boric acid treatment (b2). Notice the degenerative changes within the zoosporangia and absence of spore production and release (b2; arrow).

The impact of boric acid on maturation of young *Saprolegnia* zoosporangia was further investigated. It was found that boric acid interferes with the production and subsequent release of zoospores. Vacuolation of the entire of zoosporangia was the most prominent sign observed after treatment (FIG. 2).

Example 3

Post-Treatment Spore Release is Dependent on Length of Exposure to BA

*Saprolegnia* spores and zoosporangia were treated with boric acid at 1 g/L (diluted in SAW) for various time periods, 12, 24, 48, 72 and 96 h. At indicated time points BA was replaced with SAW. The ability of treated spores to germinate and colonize sesame seeds was recorded 24 h following the treatment removal. Treated zoosporangia were also examined for their ability to release spore. Spores and zoosporangia in SAW were used as a non-treated control. Results were confirmed with fluorescent microscopy using SYTO 9 dye (Invitrogen®) 5 mM solution in DMSO.

Two strains of *Saprolegnia* spp. (*S. diclina* VIO 2739 and *S. parasitica* VIO 2741) were used for in vivo testing. Both strains had previously been proved to be pathogenic for salmon eggs. Cysts were produced according to the method described earlier. The cysts were counted using a haemocytometer. The cyst suspensions were adjusted by dilution to obtain the required density $1.0 \times 10^4$ spores/L.

Atlantic salmon eyed eggs with an age of 385 degrees days post fertilization when received at the laboratory. All batches of eggs were formalin treated as standard procedure during incubation, and disinfected with buffodine (1:100, 10 min) before shipment. Temperature range during incubation was 2.4-8.0° C.; average: 4.2° C. The parent population had been screened for infection with salmon pancreas disease virus (causing pancreas disease), infectious salmon anemia virus (causing ISA) and for *Renibacterium salmoninarum* (causing bacterial kidney disease). After arrival to the laboratory aquaria eggs were transferred to an incubator which was supplied with continuous water flow (0.8 L/min per liter of eggs) with water temperature ranging from 5 to 7° C. To avoid mortality from transportation damage, eggs were acclimatized for 3 days before they were used in the experiment.

Groups of live eyed salmon eggs were killed by immersion for one min in water bath at temperature of 60° C. Dead eggs were incubated in 24-well microwell plates with *Saprolegnia* spore suspensions, $1.0 \times 10^4$ spores/L at 15° C. for 48 h. Incubated eggs were examined microscopically for the presence of *Saprolegnia* hyphae.

Three different challenge experiments were performed on salmon eggs and one on salmonid yolk sac fry obtained from the hatched eggs as described below.

In this experiment, the safety of continuous exposure of live eggs to different concentration of BA was tested. In addition, the activity of BA with regard to its ability to control the spread of *Saprolegnia* sp. infection between eyed salmon eggs was tested. The setup allowed to determine the optimal BA concentration that is safe for eyed eggs and at the same time able to control the spread of infection between eggs.

About 730 live eggs were used in this experiment. They were divided in to 9 main groups and tested in seven different BA concentrations plus two controls as described below. Each group was subdivided into 3 replicates of 27±2 eggs. Live eggs were challenged by co-incubation with infected dead ones (three infected dead eggs/replicate). Eggs were placed in a container to form an even layer (1 egg layer) and to be in close contact with the source of infection. To control the incubation temperature, all the containers with different BA concentrations tested and the controls were kept in a water bath with continuous water flow. Each container was supplied with an aerator. Water temperature during the experimental period ranged from 4-7° C., the pH ranged from 6.8-7.0.

In all treated groups, eggs were exposed to BA continuously until most of the eggs were hatched. BA treatment was tested at the following concentrations; 0.2, 0.4, 0.6, 0.8, 1.0, 1.2, 1.4 g/L. PA concentrations ranged from 0.2-1.0 g/L.

During the experiments no negative impact with regard to hatchability and viability was observed in either eggs or fry, which indicate safety of use at all tested concentrations. The high hatchability and survival rates recorded following the in vivo testing suggest that boric acid is a candidate for prophylaxis and control of saprolegniosis.

Eggs incubated in aquarium water were used as non-treated negative controls and those exposed to bronopol (Pyceze®) served as positive controls. Eggs were examined every day for attachment between the infected dead eggs and live ones, presence of any dead eggs, time of egg hatching, hatching rate and the presence of any fry abnormalities as described.

Figure 3:
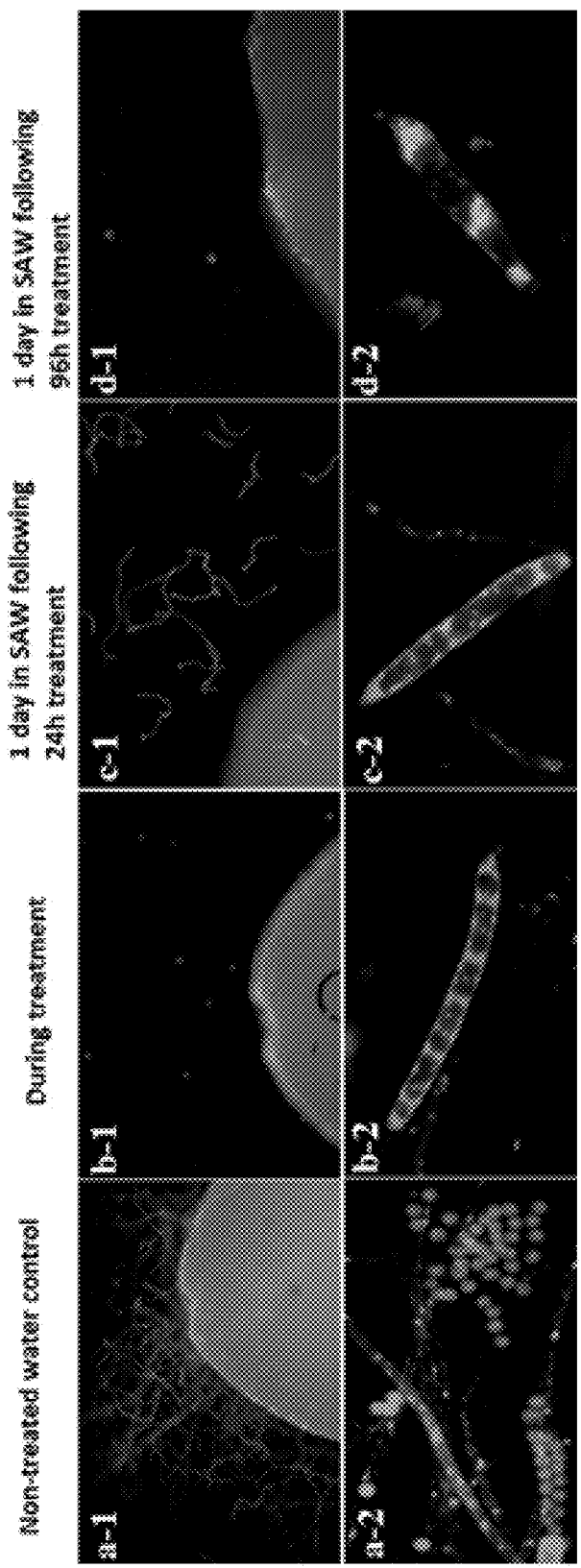
FIG. 3 is fluorescence microscopy showing the viability of boric acid treated *Saprolegnia* spores and zoosporangia with SYTO 9 stain.

FIG. 3 is a fluorescence microscopy showing the viability of boric acid treated *Saprolegnia* spores and zoosporangia with SYTO 9 stain. FIG. 3*a*-1) Colonization is seen on control seed. FIG. 3*a*-2) Normal zoosporangium sporulating. FIG. 3*b*-1) Non-colonized seed during treatment. FIG. 3*b*-2) Effect on zoosporangium during treatment. FIGS. 3*c*-1 and *c*-2) Growing hyphae were treated for 24 h with BA and left in SAW for another 24 h after treatment was terminated. Thin hyphae can be seen projecting out from seeds in *c*-1. FIG. 3*c*-2 shows a close-up of zoosporangium treated as in FIG. 3*c*-1. FIGS. 3 *d*-1 and *d*-2) Growing hyphae were treated for 96 h in BA and then left in SAW for 24 h after treatment was terminated. There is no colonization on seeds after 96 h BA treatment and the zoosporangium FIG. 3(*d*-2) appears with condensed staining and a thin wall.

It was also tested to see whether treated zoosporangia would release spores after treatment was terminated and different exposure times to BA were tested. Some zoosporangia that were treated with BA for 12 and 24 h showed spore release 24 h after exposure had been terminated (Table 2, FIG. 3*b*). In contrast, in samples exposed to BA for 72 and 96 h no spore release was shown (FIG. 3*c*). Massive spore release was recorded in the non-treated control group (FIG. 3*a*).

Continuous treatment with BA prevents infection of fertilized eggs at concentration above 0.2 g/L. The co-incubation method was used where live eggs were challenged by introducing killed and experimentally infected dead into the trays. The concentrations used ranged from 0.2 to 1.4 g/L with an incremental increase of 0.2 g/L between groups (7 in total). Three infection foci were used per replicate.

In the non-treated controls and 3 days after introduction of the infected, dead egg, the hyphae started growing out from infected dead eggs and colonized live surrounding eggs. In the BA treated groups no colonization was observed.

On day 5 post challenge, eggs in the non-treated groups started to coalesce and formed a one-unit appearance of dead eggs, completely covered with *Saprolegnia* mycelium. Still no sign of infection was observed in the treated groups, and no dead eggs were observed. In the group treated with BA at 0.2 g/L, one infection focus was found with slight attachment between two live eggs and infected dead egg. On day 7 post challenge, eggs started to hatch in the non-treated group and some of the treated groups (0.4 and 1.2 g/L). The eggs in the groups treated at concentrations 0.2, 0.6, 0.8, 1.0 and 1.4 g/L hatching started 1 day later.

Results obtained during the second week were similar to what seen during the first week where no infection was recorded in any of the concentrations tested except 0.2 g/L. At this concentration, slight attachment was observed between the egg-shell of the live eggs and the infected dead egg (source of infection). This did not cause the foetus to die as eggs hatched and yolk sac fry swam away from the eggshell.

Figure 4:
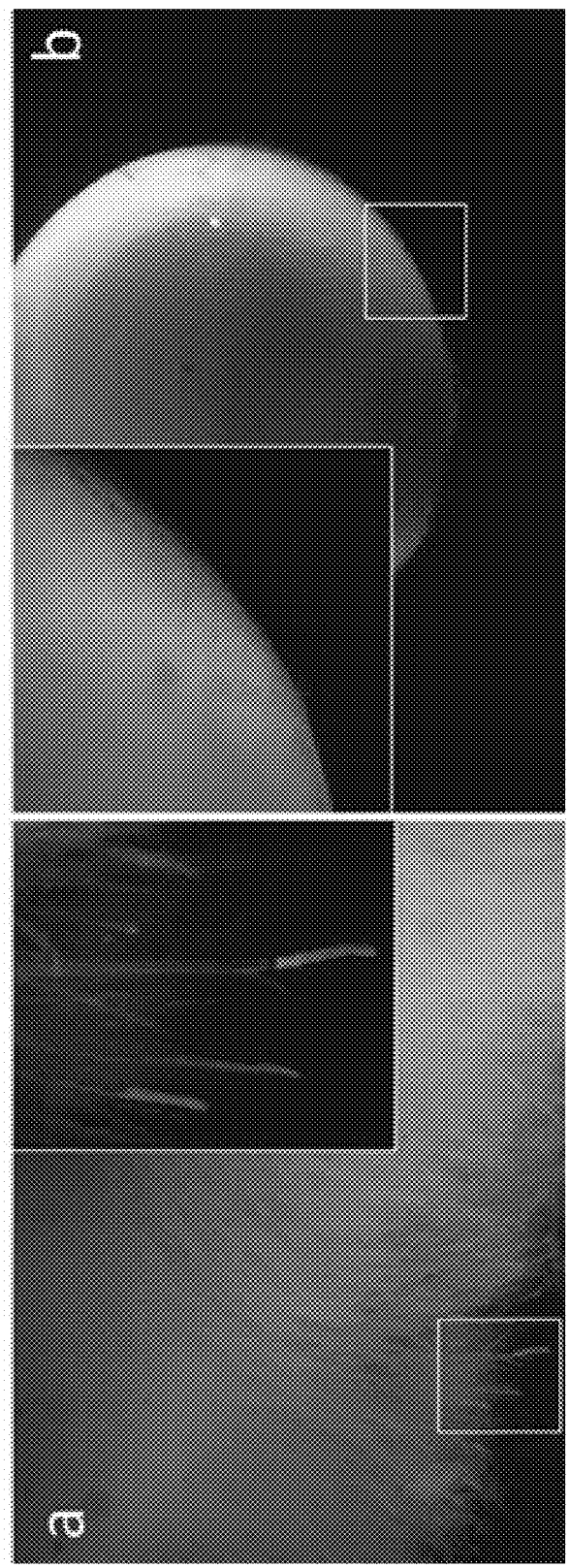
FIG. 4 shows microscopical examination of infected dead eggs used as a source of infection after the termination of the continuous exposure experiment. Mature *Saprolegnia* zoosporangium (a) in the non-treated control group compared to treated one exposed continuously to boric acid treatment (0.6 g/L) (b).
Figure 5:
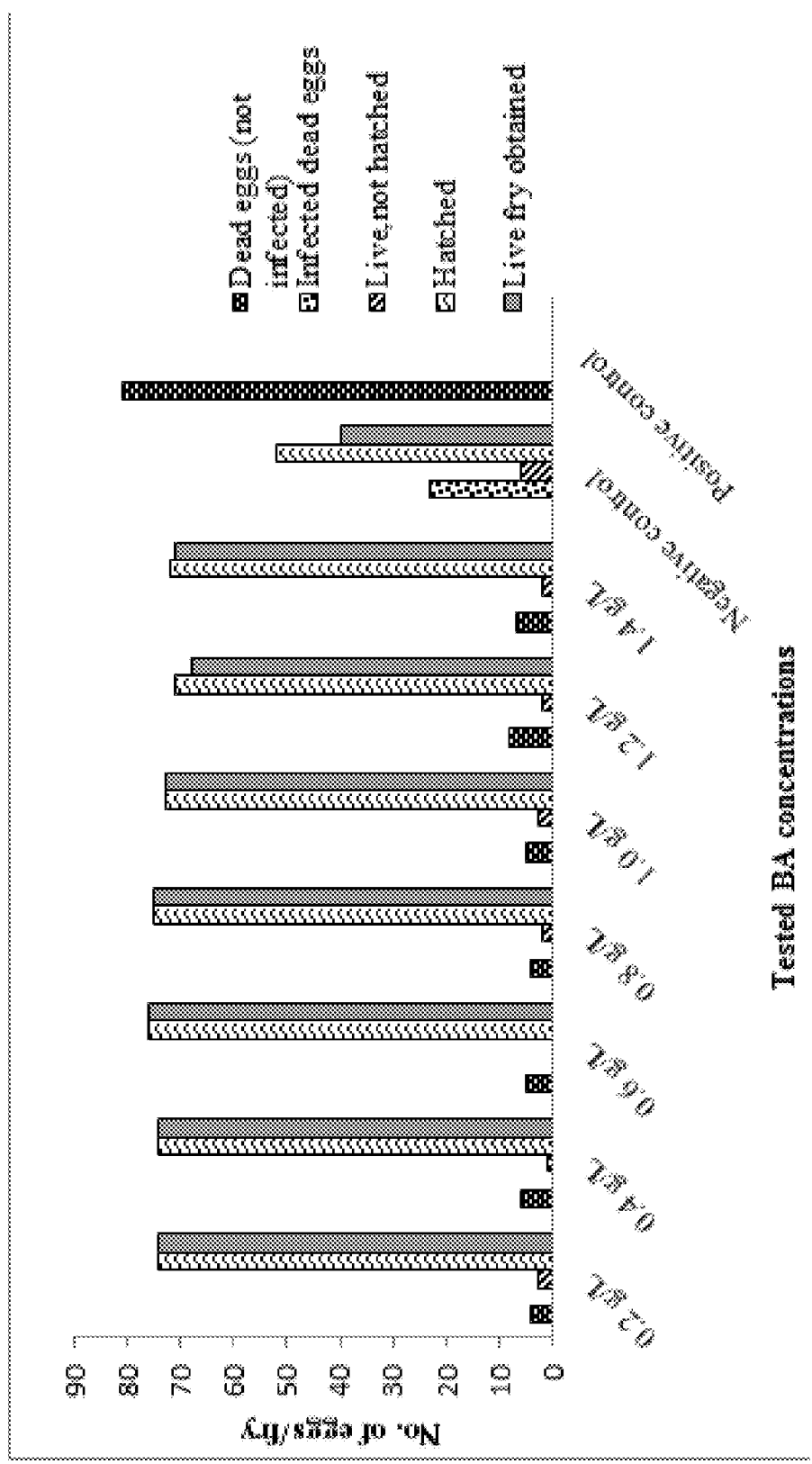
FIG. 5 illustrates mortality, infection, hatching rates and fry viability in boric acid treated groups and controls at the end of the first experiment (Continuous exposure).

At the end of the experiment and in groups treated at BA concentration<0.2 g/L the mycelium covering the eggs that were used as source of infection was scant, while many infected dead eggs were detected in the non-treated control group (FIG. 4). The numbers of dead, hatched, and infected eggs and live fry were recorded after the termination of the experiment (FIG. 5). The bronopol treated group (positive control) showed 100% mortality after 2 hour continuous exposure (FIG. 5).

Example 4

Intermittent Exposure with BA Prevents Infection of Dead Eggs

The effect of intermittent exposure to BA with regard to its ability to control the spread of *Saprolegnia* sp. infection between eyed salmon eggs was also tested. The experimental design was as described in experiment 1 with the same number of eggs per replicate (N=27±2) and the number of infected eggs introduced per replicate (3 per 27 eggs). The difference was that the eggs were exposed to higher BA concentrations (1, 2, 3, 4 g/L) for 4 h once a day over the course of the experiment which lasted for 14 days in total. After 4 h of treatment the flow of aquarium water was resumed. The same treatment was applied 24 h later and every day up to 14 days. The time between treatments was the same throughout the experiment. The number of dead eggs, presence or absence of infection and hatching rates were recorded over the duration of the experiment.

Infected dead eggs that were used as source of infection in the BA treated groups and the non-treated control were examined microscopically to observe the effect of BA treatment on the growing mycelia.

The ability of BA to protect dead eggs from becoming infected with *Saprolegnia* spores was investigated. The rationale is that dead eggs may be the first to get infected under natural conditions and act as a source of infection for live eggs. Combined treatment of BA and PA was also tested.

Five egg groups were used, each group divided equally into 3 smaller sub-groups. 25 live eggs plus 5 dead ones were placed in each of the sub-groups (90 eggs per group). Dead eggs were prepared as described in (2.3.3). In the groups, eggs were supplied with continuous slow water flow of 1 L/min. The aquarium water at the facilities of the Norwegian Veterinary Institute/Norwegian School of Veterinary Science contains *Saprolegnia* zoospores and was used as source of infection. In addition, to ensure presence of *Saprolegnia* spores in the in-coming water, growing mycelia from *S. diclina* (VIO 2739) and *S. parasitica* (VIO 2741) were packed in a piece of gauze and fixed inside the main tubes that supplied the water to all containers. Treatment with BA was carried out as follows. The water flow was stopped and each group, except the non-treated control group, was treated with BA at concentrations of 1, 2, 3, and 4 g/L. The treatment period was 4 hours/day after which water flow was resumed. Dead eggs were inspected daily over 14 days for their colonization with *Saprolegnia* spores and the presence of growing hypha. Number of dead eggs per group and hatching rates were recorded.

The safety of continuous exposure of salmon fry to a low concentration of BA (0.5 g/L) was also investigated to understand what extent BA will protect Atlantic salmon fry from becoming infected by *Saprolegnia* spores during a natural outbreak of saprolegniosis in the aquarium.

About 330 live, yolk-sac fry of Atlantic salmon obtained from treated hatched eggs were used in this experiment. They were divided into two equal groups. Group 1 was kept in aquarium water naturally containing virulent *Saprolegnia* spores. Group 2 was put on continuous treatment with BA at a concentration of 0.5 g/L. The containers were supplied with air through air pumps. Fry were observed daily and the numbers of dead fry per day were recorded in both groups. To confirm whether the high mortality rates were due to *Saprolegnia* infection, live and freshly dead fry were collected and examined from both groups by the end of the experiment. They were examined microscopically and incubated on glucose yeast agar with antibiotics. Plates were kept at 20° C. for 24 h and examined for the presence of *Saprolegnia* mycelia.

Figure 6:
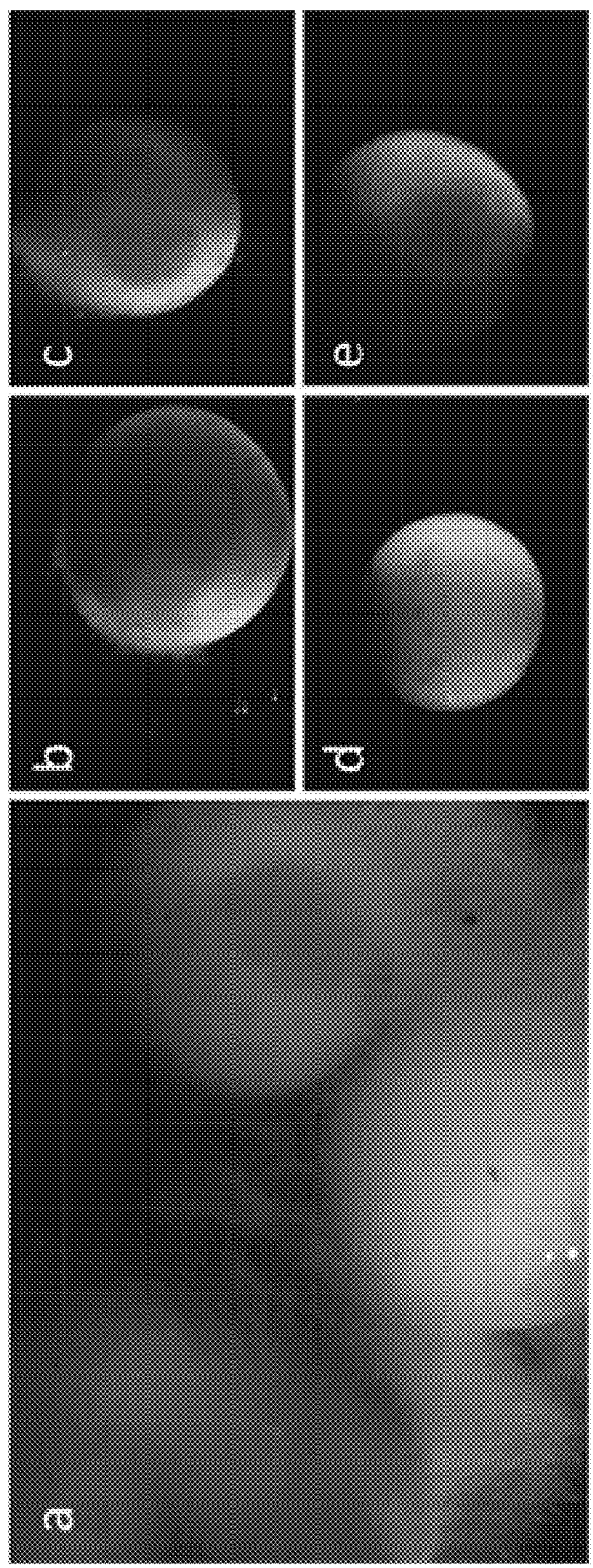
FIG. 6 shows microscopical examination of the infected dead eggs, used as a source of infection, by the end of the intermittent exposure experiment.

FIG. 6 demonstrates microscopical examination of the infected dead eggs, used as a source of infection, by the end of the intermittent exposure experiment. Non-treated control group FIG. 6(*a*) compared to treated ones intermittently exposed to boric acid treatment at different concentrations FIG. 6(*b*) 1.0 g/L, (*c*) 2 g/L, (*d*) 3 g/L, (*e*) 4/L. The abundance of the growing mycelia in the non-treated control and colonization of neighboring ones result in death of the neighboring ones.

Figure 7:
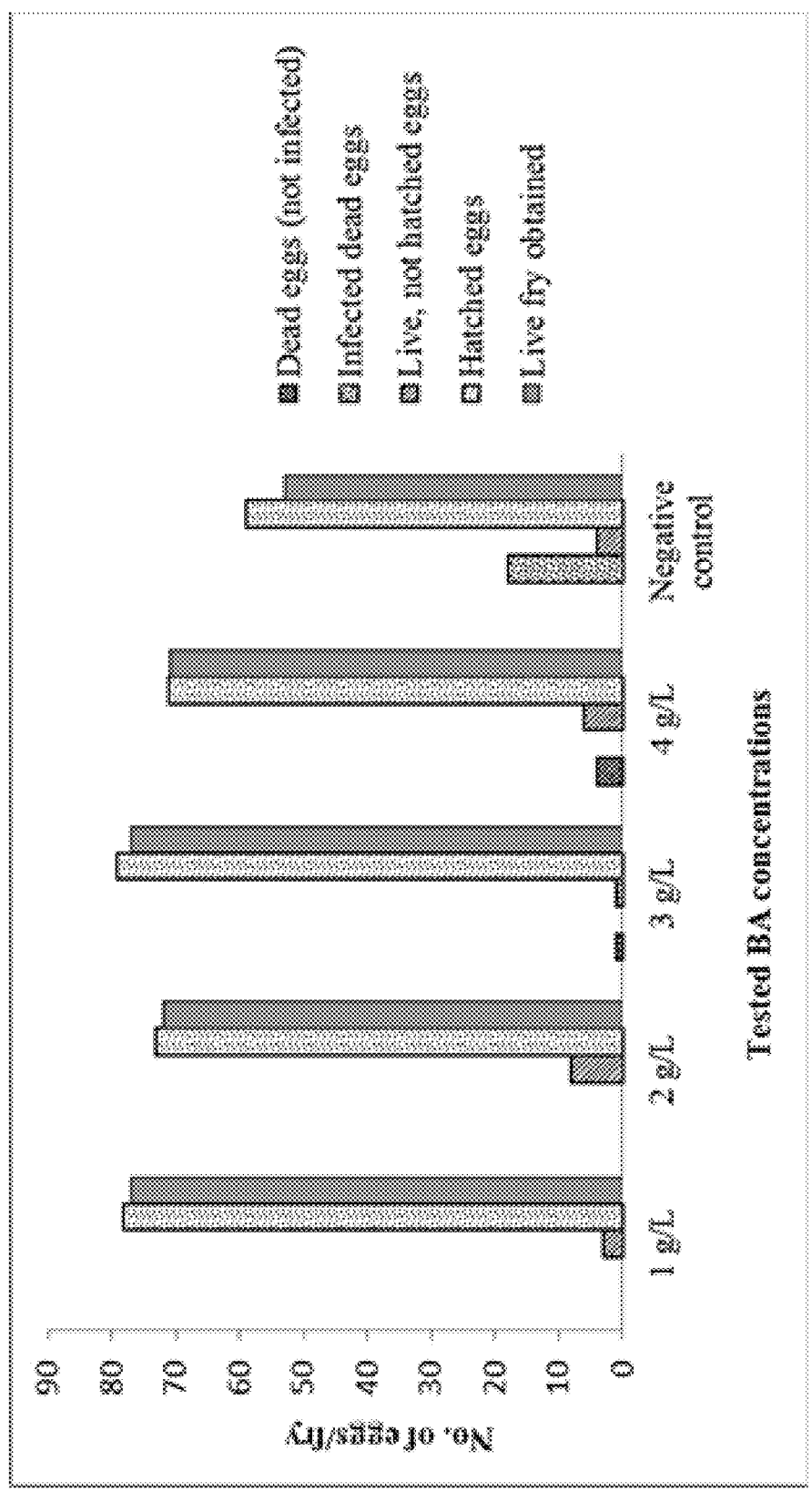
FIG. 7 illustrates mortality, infection, hatching rates and number of live fry obtained by the end of the experiment in boric acid treated groups and non-treated control in response to intermittent exposure to BA.

BA at concentrations of 1, 2, 3, or 4 g/L and exposure was included and treatment was for 4 h once a day. Many eggs in the non-treated control group died as they were colonized by *Saprolegnia* mycelia (FIG. 6*a*). Microscopically, characteristic *Saprolegnia* zoosporangia were observed with release of motile zoospores. No hyphal attachment between infected dead and live eggs were observed at any of the concentrations tested (FIG. 6*b*-6*e*). Dead eggs that were used as a source of infection in all treated groups showed scanty attachment of mycelium. When examined microscopically, only remnants of mycelia mixed with some organic debris from the water were seen. FIG. 7 shows the numbers of dead, hatched and infected eggs, and number of live fry obtained after termination of the experiment. These results indicate that BA can be used for the treatment of natural infection in yolk sac fry.

Figure 8:
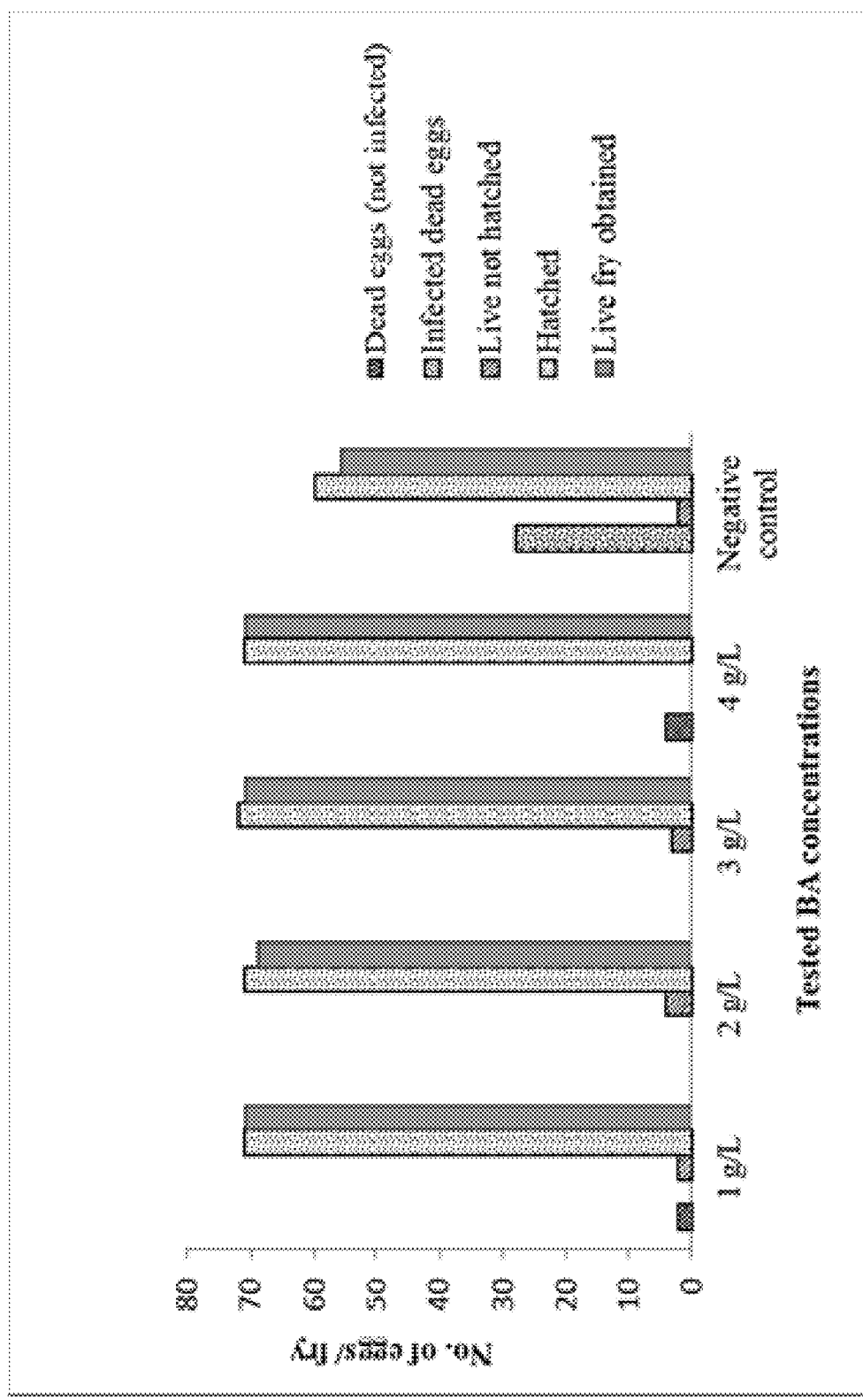
FIG. 8 illustrates mortality, infection, hatching rates and fry viability in egg groups intermittently exposed to boric acid (third experiment) compared to non-treated control in response to intermittent exposure to BA.

Daily treatment with BA protect against *Saprolegnia* infection of dead eggs. No hyphal growth was observed on dead eggs in any of the treated groups (1-4 g/L) and subsequently no attachment was found between dead and live eggs. In the water control group, growing *Saprolegnia* mycelia were detected on the dead eggs by the fifth day after challenge. At later stages, the growing mycelia from the dead eggs showed more pronounced growth and penetrated the surrounding live eggs. By the end of the experiment (day 14) the number of dead, infected eggs and hatching rate were recorded (FIG. 8).

Figure 9:
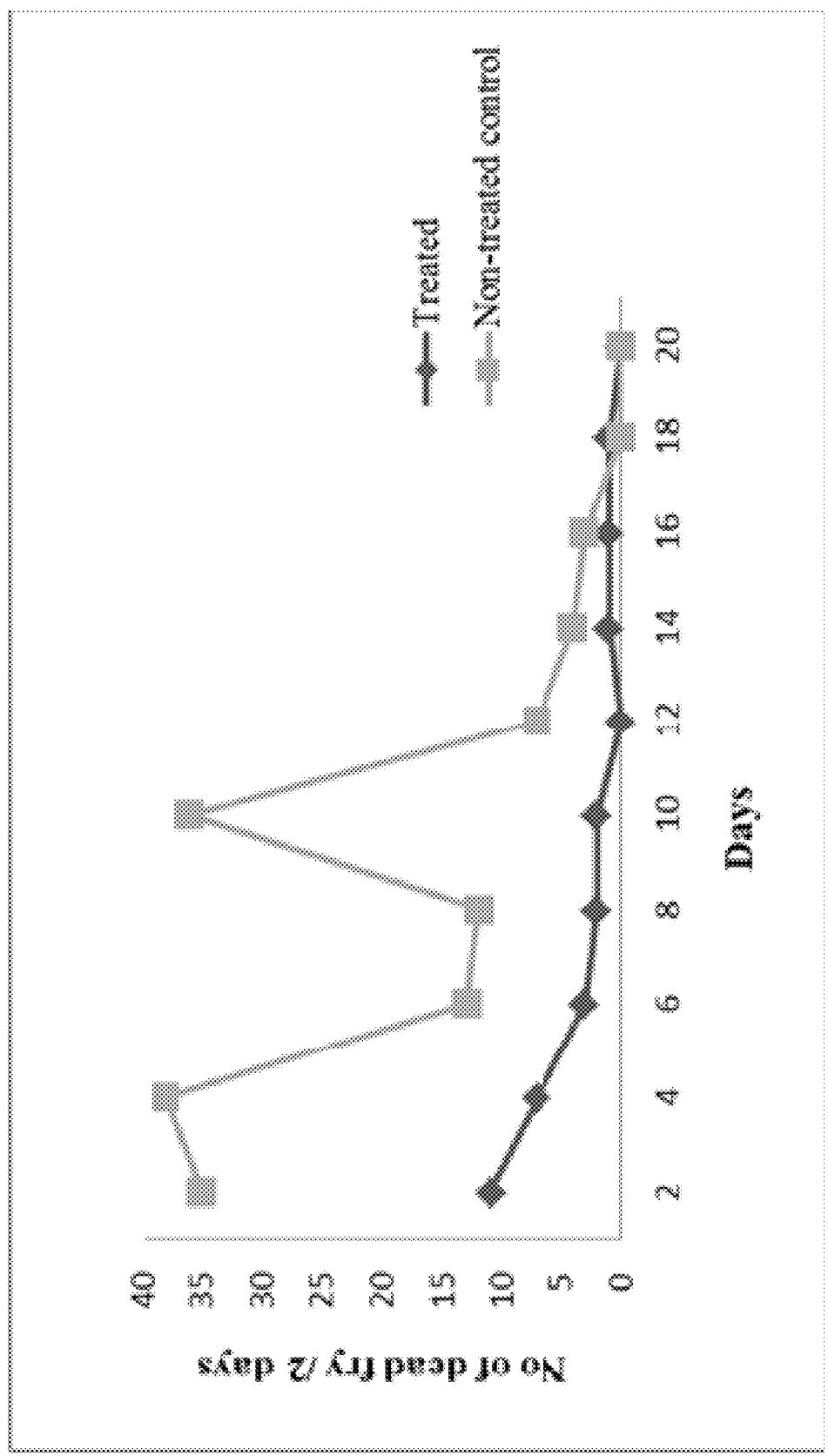
FIG. 9 illustrates mortality patterns recorded every other day among treated salmonid yolk sac fry and control ones during the outbreak of saprolegniosis.
Figure 10:
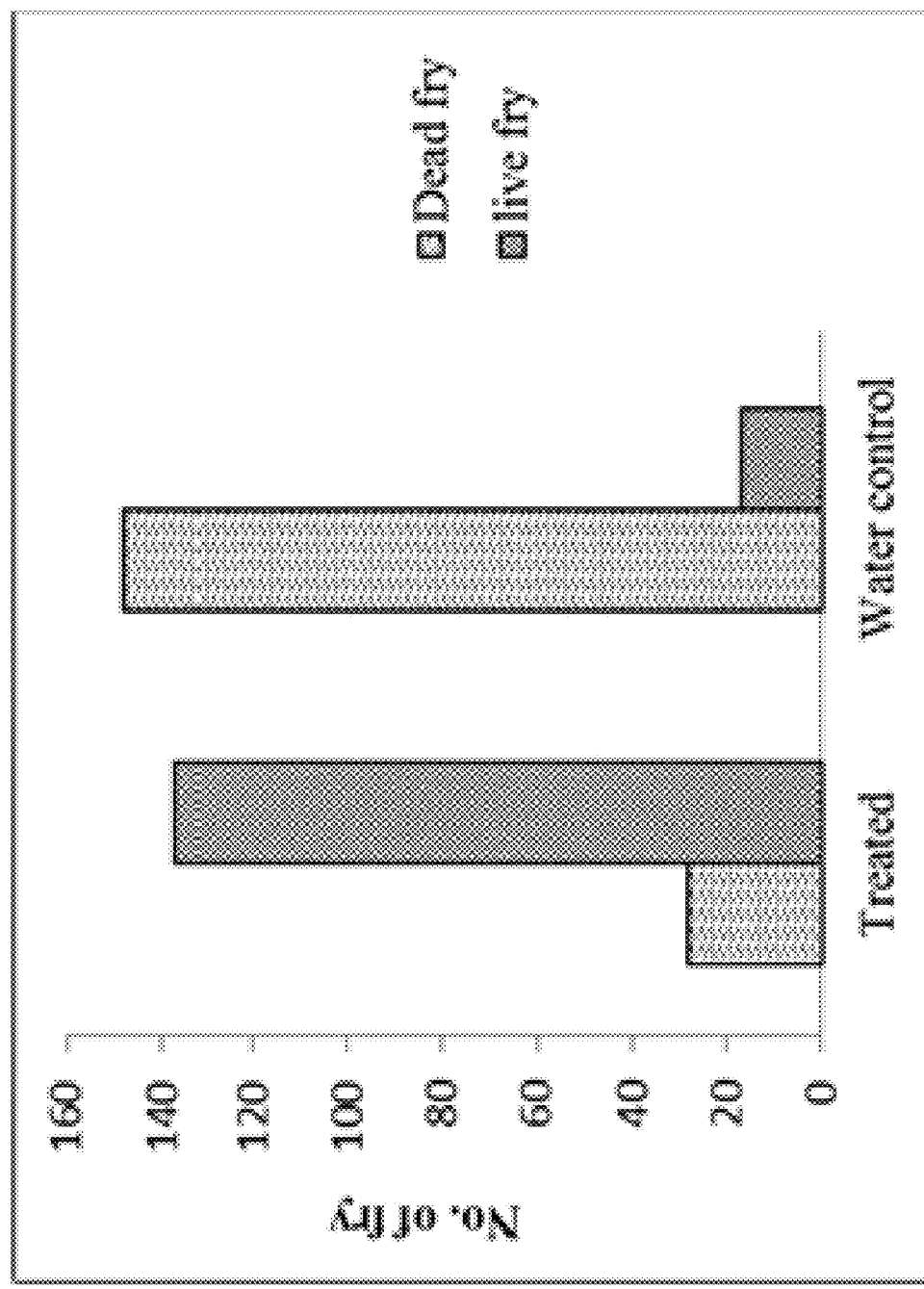
FIG. 10 illustrates cumulative mortalities in salmonid yolk sac fry in both boric acid treated and non-treated control groups by the end of the natural outbreak of saprolegniosis.

Continuous treatment with BA protect yolk sac fray against natural infection. Significant reduction in fry mortality rates (FIGS. 9 and 10) was observed in the BA treated group compared to the non-treated control. Dead fry were completely covered with *Saprolegnia* mycelia. Microscopical examination revealed tufts of white mycelia causing gill obstruction of live and freshly dead fry in the non-treated control group. The characteristic *Saprolegnia* zoosporangia were also observed microscopically. Results were confirmed with isolation on GY agar and broth.

Exemplary Embodiments

1. A method for administering an anti-microorganism composition to an aquatic animal to treat chitin-containing microorganism infection or colonization, the method comprising:
dissolving an anti-microorganism composition in a carrier to provide an anti-microorganism solution, the anti-microorganism composition including boric acid (BA); and
contacting an aquatic animal with the anti-microorganism solution.

2. A kit for administering an anti-microorganism composition to an aquatic animal to treat chitin-containing microorganism infection or colonization, the kit comprising:
a container having the anti-microorganism composition including boric acid (BA), the anti-microorganism composition dissolvable in a carrier to provide an anti-microorganism solution; and
package material that includes an instruction directing administering of the anti-microorganism composition to the aquatic animal to treat the chitin-containing microorganism infection or colonization.

3. The method or kit of any one of embodiments 1 and 2, wherein the aquatic animal is selected from the group consisting of a fish, an aquatic mammal, an aquatic bird, an aquatic reptile, an amphibian, and an aquatic invertebrate.

4. The method or kit of any one of embodiments 1 and 2, wherein the aquatic animal is a fish.

5. The method of embodiment 4, wherein the fish is a farmed fish including at least one of a brown trout, an Atlantic salmon, a rainbow trout, a coho salmon, a channel catfish, a pike, an arctic char, an eel, a roach, a carp, a sturgeon, a kissing gourami, a guppy, a swordfish, or a platyfish.

6. The method of embodiment 4, wherein the fish includes at least one of a fish egg, a Juvenile fish, a fry, a fingerling, an adult fish or an off-spring of the fish.

7. The method or kit of any one of embodiments 1 and 2, wherein the aquatic animal has the chitin-containing microorganism infection or colonization.

8. The method or kit of any one of embodiments 1 and 2, wherein the chitin-containing microorganism infection is associated with an oomycete including at least one of a *Saprolegnia*, an *Aphanomyces*, or a *Branchiomyces*.

9. The method or kit of any one of embodiments 1 and 2, wherein the chitin-containing microorganism infection is associated with a *Saprolegnia*.

10. The method or kit of any one of embodiments 1 and 2, wherein the chitin-containing microorganism infection is associated with an ectoparasites.

11. The method of embodiment 10, wherein the ectoparasites comprises a sea louse.

12. The method of embodiment 11 wherein the sea louse is a sea louse of at least one of a genera *Lepeophtheirus, Caligus, Caligus rogercresseyi, Caligus clemensi, Caligus chiastos, Caligus epidemicus, Caligus elongates*, or *Lepeophtheirus salmonis*.

13. The method or kit of any one of embodiments 1 and 2, wherein the BA in the anti-microorganism solution has a concentration in the anti-microorganism solution of between about 0.2 g/L and about 1 g/L.

14. The method or kit of any one of embodiments 1 and 2, wherein the BA in the anti-microorganism solution has a concentration in the anti-microorganism solution of between about 0.1 g/L and about 0.2 g/L.

15. The method or kit of any one of embodiments 1 and 2, wherein the BA in the anti-microorganism solution has a concentration in the anti-microorganism solution that is not less than about 0.2 g/L.

16. The method or kit of any one of embodiments 1 and 2, wherein the BA in the anti-microorganism solution has a concentration in the anti-microorganism solution of between about 0.2 g/L and about 0.5 g/L.

17. The method or kit of any one of embodiments 1 and 2, wherein the BA in the anti-microorganism solution has a concentration in the anti-microorganism solution of between about 0.5 g/L and about 1 g/L.

18. The method of any one of embodiments 13-17, wherein the anti-microorganism solution contains propionic acid (PA), and a concentration of the PA in the anti-microorganism solution of not less than about 0.2 g/L.

19. The method of any one of embodiments 13-17, wherein the anti-microorganism solution contains propionic acid (PA), and a concentration of the PA in the anti-microorganism solution of between about 0.2 g/L and about 1 g/L.

20. The method or kit of any one of embodiments 1 and 2, wherein the contacting the aquatic animal with the anti-microorganism solution comprises contacting the aquatic animal with the anti-microorganism solution for a period of time of between about 24 hours and about 96 hours.

21. The method or kit of any one of embodiments 1 and 2, wherein the contacting the aquatic animal with the anti-microorganism solution comprises contacting the aquatic animal with the anti-microorganism solution for a predetermined number of times within 24 hours.

22. The method of embodiment 21, wherein the predetermined number is at least one of 1, 2, 3, 4, 5, 6, or 8.

23. The method or kit of any one of embodiments 1 and 2, further comprising:
removing the aquatic animal from the anti-microorganism solution.

24. The method of embodiment 23, further comprising:
contacting the aquatic animal with water not containing the anti-microorganism composition.

25. A method for treating chitin-containing microorganism infection or colonization on an aquatic animal, the method comprising:
contacting the aquatic animal with marine or fresh water containing boric acid (BA) in a sufficient quality to inhibit proliferation of the chitin-containing microorganism.

26. A system for farming an aquatic animal, comprising:
a farming system for farming the aquatic animal, the farming system including marine or fresh water containing boric acid (BA) in a sufficient quality to inhibit proliferation of chitin-containing microorganisms.

27. The method or system of at least one of embodiments 25 and 26, wherein the aquatic animal is selected from the group consisting of a fish, an aquatic mammal, an aquatic bird, an aquatic reptile, an amphibian, and an aquatic invertebrate.

28. The method or system of at least one of embodiments 25 and 26, wherein the aquatic animal is a fish.

29. The method or system of embodiment 28, wherein the fish is a farmed fish including at least one of a brown trout, an Atlantic salmon, a rainbow trout, a coho salmon, a channel catfish, a pike, an arctic char, an eel, a roach, a carp, a sturgeon, a kissing gourami, a guppy, a swordfish, or a platyfish.

30. The method or system of embodiment 28, wherein the fish including at least one of a fish egg, a Juvenile fish, a fry, a fingerling, an adult fish, or an off-spring of the fish.

31. The method or system of at least one of embodiments 25 and 26, wherein the aquatic animal has the chitin-containing microorganism infection or colonization.

32. The method or system of at least one of embodiments 25 and 26, wherein the chitin-containing microorganism comprises an oomycete.

33. The method or system of embodiment 32, wherein the oomycete comprises at least one of a *Saprolegnia*, an *Aphanomyces*, or a *Branchiomyces*.

34. The method or system of at least one of embodiments 25 and 26, wherein the chitin-containing microorganism comprises a *Saprolegnia*.

35. The method or system of at least one of embodiments 25 and 26, wherein the chitin-containing microorganism infection is associated with a sea louse.

36. The method or system of embodiment 35, wherein the sea louse is a sea louse of at least one of a genera *Lepeophtheirus, Caligus, Caligus rogercresseyi, Caligus clemensi, Caligus chiastos, Caligus epidemicus, Caligus elongates*, or *Lepeophtheirus salmonis*.

37. The method or system of at least one of embodiments 25 and 26, wherein the BA in the marine or freshwater has a concentration of between about 0.2 g/L and about 1 g/L.

38. The method or system of at least one of embodiments 25 and 26, wherein the BA in the marine or freshwater has a concentration of between about 0.1 g/L and about 0.2 g/L.

39. The method or system of at least one of embodiments 25 and 26, wherein the BA in the marine or freshwater has a concentration not less than about 0.2 g/L.

40. The method or system of at least one of embodiments 25 and 26, wherein the BA in the marine or freshwater has a concentration of between about 0.2 g/L and about 0.5 g/L.

41. The method or system of at least one of embodiments 25 and 26, wherein the BA in the marine or freshwater has a concentration of between about 0.5 g/L and about 1 g/L.

42. The method or system of any one of embodiments 37-41, wherein the marine or freshwater contains PA, and a concentration of PA in the marine or freshwater of about 0.2 g/L.

43. The method or system of any one of embodiments 37-41, wherein the marine or freshwater contains propionic acid (PA), and a concentration of PA in the marine or freshwater of between about 0.2 g/L and about 1 g/L.

44. The method or system of at least one of embodiments 25 and 26, wherein the contacting the aquatic animal with the marine or freshwater containing the BA comprises contacting the aquatic animal with the marine or freshwater containing the BA for a period of time of between about 24 hours and about 96 hours.

45. The method or system of at least one of embodiments 25 and 26, wherein the contacting the aquatic animal with the marine or freshwater containing the BA comprises contacting the aquatic animal with the marine or freshwater containing the BA for a predetermined number of times within 24 hours.

46. The method or system of embodiment 45, wherein the predetermined number is at least one of 1, 2, 3, 4, 5, 6, or 8.

What is claimed is:

1. A method for administering an anti-microorganism composition to a fish or fertilized eggs of the fish to inhibit germination and colonization of a chitin-containing microorganism on the fish or the fertilized eggs of the fish, the method comprising:
    dissolving an anti-microorganism composition in a carrier to provide an anti-microorganism solution, the anti-microorganism composition including boric acid (BA), a concentration of the BA in the anti-microorganism solution not less than about 0.2 g/L; and
    contacting the fish or fertilized eggs of the fish with the anti-microorganism solution, wherein the fish or the fertilized eggs of the fish is the fertilized eggs of the fish.

2. The method of claim 1, wherein the fish is a farmed fish including at least one of a brown trout, an Atlantic salmon, a rainbow trout, a coho salmon, a channel catfish, a pike, an arctic char, an eel, a roach, a carp, a sturgeon, a kissing gourami, a guppy, a swordfish, or a platyfish.

3. The method of claim 1, wherein the infection or colonization of chitin-containing microorganism is associated with an oomycete including at least one of a *Saprolegnia*, an *Aphanomyces*, or a *Branchiomyces*.

4. The method of claim 1, wherein the infection or colonization of the chitin-containing microorganism is associated with an ectoparasite.

5. The method of claim 4, wherein the ectoparasites comprises a sea louse.

6. The method of claim 1, wherein the anti-microorganism solution further contains propionic acid (PA), and wherein a concentration of the PA in the anti-microorganism solution is not less than about 0.2 g/L.

7. The method of claim 1, wherein the contacting the fish or the fertilized eggs of the fish with the anti-microorganism solution comprises contacting the fish or the fertilized eggs of the fish with the anti-microorganism solution for a period of time of between about 24 hours and about 96 hours.

8. The method of claim 1, further comprising:
    removing the fish or the fertilized eggs of the fish from the anti-microorganism solution; and
    contacting the fish or the fertilized eggs of the fish with water not containing the anti-microorganism composition.

9. The method of claim 1, wherein the contacting the fish or the fertilized eggs of the fish with the anti-microorganism solution comprising contacting the fish or the fertilized eggs of the fish with the anti-microorganism solution at a temperature range from 2.4 to 8.0° C.

* * * * *